United States Patent
Wang et al.

(10) Patent No.: US 9,903,853 B2
(45) Date of Patent: Feb. 27, 2018

(54) METHOD FOR MEASURING FREE RADICAL BASED ON CONDUCTIVITY CHANGE OF CONDUCTIVE POLYMER

(71) Applicant: National Tsing Hua University, Hsinchu (TW)

(72) Inventors: Yu-Lin Wang, Hsinchu (TW); Jung-Ying Fang, Hsinchu (TW); Chia-Ho Chu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 61 days.

(21) Appl. No.: 14/563,679

(22) Filed: Dec. 8, 2014

(65) Prior Publication Data

US 2016/0084783 A1 Mar. 24, 2016

(30) Foreign Application Priority Data

Sep. 22, 2014 (TW) .............................. 103132566 A

(51) Int. Cl.
 *G01N 27/00* (2006.01)
 *G01N 33/487* (2006.01)
 *G01N 27/12* (2006.01)

(52) U.S. Cl.
 CPC ..... *G01N 33/48707* (2013.01); *G01N 27/126* (2013.01)

(58) Field of Classification Search
 CPC ............. G01N 27/04; G01N 33/48707; G01N 33/487; G01N 27/126
 See application file for complete search history.

(56) References Cited

U.S. PATENT DOCUMENTS

| | | | | |
|---|---|---|---|---|
| 5,798,271 A | * | 8/1998 | Godec | G01N 27/06 422/78 |
| 2004/0221401 A1 | * | 11/2004 | Desenne | A61K 8/365 8/405 |
| 2008/0289960 A1 | * | 11/2008 | Yuasa | C25D 5/00 204/416 |
| 2010/0122713 A1 | * | 5/2010 | Tanaka | A23B 7/152 134/26 |

(Continued)

FOREIGN PATENT DOCUMENTS

JP 2007-302913 * 11/2007 ............... C25D 9/12

*Primary Examiner* — Jeff Natalini
(74) *Attorney, Agent, or Firm* — Muncy, Geissler, Olds & Lowe, P.C.

(57) ABSTRACT

A method for measuring free radical comprises providing a sensor including a substrate and a conductive polymer layer, wherein the conductive polymer layer is configured on the substrate and made of conductive polymer; applying a liquid sample with free radical to the sensor so that the conductive polymer layer is covered with the liquid sample and the conductivity of the conductive polymer layer is lowered due to oxidation of the conductive polymer by free radical; and calculating the concentration of the free radical in the liquid sample based on the conductivity change rate of the conductive polymer before and after the liquid sample is applied to the conductive polymer. The present invention has advantages including low cost, small size, and ease of operation, which make it a good candidate for detecting hydroxyl radicals for oxidative stress studies.

10 Claims, 8 Drawing Sheets

(56) References Cited

U.S. PATENT DOCUMENTS

2011/0210077 A1* 9/2011 Coulter .................. C02F 1/008
 210/739
2014/0095102 A1* 4/2014 Potyrailo ............... G01R 27/28
 702/127

* cited by examiner

METHOD FOR MEASURING FREE RADICAL BASED ON CONDUCTIVITY CHANGE OF CONDUCTIVE POLYMER

BACKGROUND OF THE INVENTION

1. Field of the Invention

The present invention relates to a method for measuring free radical, particularly to a method for measuring free radical based on conductivity change of conductive polymer.

2. Description of the Prior Art

Oxidative stress is currently an important research topic and is believed to be relevant to tumors, cancers, Parkinson's disease, and aging. Oxidative stress is induced by reactive oxygen species (ROS), including hydrogen peroxide ($H_2O_2$), hydroxyl radical (OH.), superoxide anion ($O_2.^-$) and singlet oxygen ($O_2.$).

Hydroxyl radical was reported to be the most reactive free radical. Hydroxyl radical was found to be able to damage DNA, RNA, proteins and lipids, leading to abnormal cell response and cell apoptosis in physiological and pathological environment. Hydroxyl radicals can be generated by Fenton reaction or Haber-Weiss reaction in vivo. Among these ROS, hydrogen peroxide is much easier to be detected due to its longest life-time. However, detecting radicals, especially for hydroxyl radicals, is challenging due to its very short life-time (~μs).

Several techniques are utilized to detect hydroxyl radicals. Electron spin resonance spectroscopy (ESR) is a typical technique, which can detect molecules with unpaired electron by characterizing the electron paramagnetic spectrum. However, the life-time of hydroxyl radicals is too short to be detected directly by ESR. Instead, a spin trap molecules, such as 5,5-dimethyl, 1-pyrroline N-oxide (DMPO), is employed to bind with hydroxyl radicals to form a complex, which is still a radical but has a longer half-life to be detected by ESR.

Fluorescence spectroscopy has also frequently been used to quantify hydroxyl radicals by the oxidation of fluorescent probes with hydroxyl radicals to either enhance or quench fluorescence signals. Chemiluminescence (CL) is enhanced with the chemiluminogenic probes reacting with hydroxyl radicals. Ultraviolet-visible spectroscopy is based on the absorbance change of a probe molecule after reacting with hydroxyl radicals, such as $Br^-$, Crocin, Ferrocyanide, or Rhodamine B. High pressure liquid chromatography (HPLC) has also been employed for hydroxyl radical detection. The above mentioned techniques are currently the most commonly used methods for detecting hydroxyl radicals.

However, these techniques all require extensive instruments, and on the other hand, they also face a problem that is the degradation of probe molecules during the measurement. To effectively reduce the high cost of hydroxyl radical detection, electronic miniaturized microsensors might be good candidates for low cost detection. Electrochemical sensors and QCM sensor were reported to detect hydroxyl radicals. Compared to the typical techniques, including ESR, Fluorescence, CL, UV-Vis, and HPLC, electronic microsensors were quite few and seldom reported for free radical detection. However, due to the great advance in microfabrication technique, electronic microsensors can be very cost-effective, and in the meantime, with comparable sensitivity and limit of detection (LOD), compared to those of typical measurements. Thus, there is a great interest and demand to develop simple, cost-effective, and highly sensitive electronic microsensors for hydroxyl radical detection.

SUMMARY OF THE INVENTION

One objective of the present invention is directed to developing simple, cost-effective, and highly sensitive electronic microsensors for hydroxyl radical detection.

According to one embodiment of the present invention, a method for measuring free radical comprises providing a sensor including a substrate and a conductive polymer layer, wherein the conductive polymer layer is configured on the substrate and made of conductive polymer, wherein the conductive polymer comprises polyacetylene, polyparaphenylene, polythiophene, polyfuran, polythianaphthene or polyaniline (PANI), wherein the sensor further comprises a first electrode and a second electrode, and wherein the conductive polymer layer is electrically connected between the first electrode and the second electrode; applying a liquid sample with a free radical to the sensor so that the conductive polymer layer is covered with the liquid sample and the conductivity of the conductive polymer layer is lowered due to oxidation of the conductive polymer by the free radical; and calculating the concentration of the free radical in the liquid sample based on the conductivity change rate of the conductive polymer before and after the liquid sample is applied to the conductive polymer.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

The main principle of the present invention is directed to measuring free radical by measuring lowered conductivity rate of the conductive polymer, which is caused by free radical oxidation. As mentioned above, free radical may include reactive oxygen species (ROS) radical, including without limitation to hydroxyl radical (OH.), superoxide anion ($O_2.^-$) and singlet oxygen ($O_2.$).

Figure 1A:
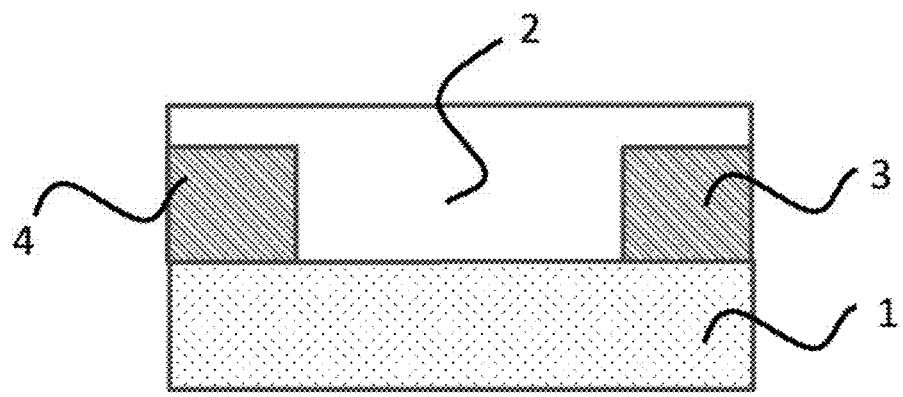
FIG. 1a illustrates a sensor according to one embodiment of the present invention.

Referring to FIG. 1a, a sensor including a substrate 1, a conductivity polymer layer 2, a first electrode 3 and a second electrode 4 is used in a method for measuring free radical of the present invention. The conductive polymer layer 2 is configured on the substrate 1 and essentially made of a conductive polymer. A liquid sample with free radical is then applied to the sensor so that the conductive polymer layer 2 is at least in contact with the liquid sample or covered with the liquid sample. The conductivity of the conductive polymer layer is lowered due to oxidation of the conductive polymer by free radical. At last, the concentration of the free radical in the liquid sample is calculated based on the conductivity change rate of the conductive polymer before and after the liquid sample is applied to the conductive polymer. Here, a first conductivity and a second conductivity of the conductive polymer layer may be measured, respectively. The first conductivity is the conductivity of the conductive polymer layer before applied with the liquid sample with free radical and the second conductivity is the conductivity of the conductive polymer layer after applied with the liquid sample with free radical, and the conductivity change rate of the conductive polymer is based on the change rate of the first conductivity and the second conductivity. For example, conductivity change rate of the conductive polymer is defined as the differential value between the first and second conductivity divided by the first conductivity.

In one embodiment, the measuring the first conductivity and the second conductivity of the conductive polymer layer is obtained by applying a bias to the conductive polymer layer and measuring the current, of the conductive polymer layer.

In the present invention, the substrate may be made of any suitable material without particular limitations. The material and size of the first and second electrode are not particularly limited as long as conductance and measurement may be achieved.

The conductive polymer of the present invention may comprise polyacetylene, polyparaphenylene, polythiophene, polyfuran, polythianaphthene or polyaniline (PANI) and the surface of the conductive polymer is modified with propane sultone. Here, in one preferred embodiment, the conductive polymer may be PANI. PANI was reported as a good radical scavenger. Hydrogen proton-doped (reduced.) PANI was proved to be able to prevent red blood cells from the attack by hydroxyl radicals, which was generated from Fenton reaction in the presence of hydrogen peroxide. Accordingly, it is possible to fabricate electronic hydroxyl radical microsensors by utilizing highly doped PANI and measuring the conductivity change of the doped-PANI after it react with hydroxyl radicals. It is believed that the doped-PANI can be oxidized by hydroxyl radicals and the oxidation of doped-PANI will result in the decreased conductivity, which can be related to the concentration of hydroxyl radicals in solutions.

The doped-PANI was spin-coated and baked on a $Si_3N_4$/Si substrate. The hydroxyl radicals were generated by Fenton reaction based on the reaction of ferrous ion and hydrogen peroxide in buffer solution. The decreased conductivity of the doped-PANI was found to be linearly dependent on the concentration of hydroxyl radicals generated by Fenton reaction. The concentration of the hydroxyl radicals were estimated and calibrated by comparing the fluorescence intensity of a dye, Amplex ultrared, oxidized by hydroxyl radicals with that of the dye oxidized by hydrogen peroxide (HRP) via the catalytic effect of HRP.

In one embodiment, the limit of detection (LOD) of this hydroxyl radical sensor is around 0.2 μM, which is comparable to those of typical measurement such as ESR or fluorescence, which mostly have the LOD around μM of hydroxyl radicals. In addition to the good LOD, the sensor only requires a small sample volume for detection. The developed hydroxyl radical microsensors have advantages including low cost, small size, and ease of operation, which make it a perfect candidate for detecting hydroxyl radicals for oxidative stress studies.

The present invention is further illustrated by the following working examples, which should not be construed as further limiting.

Preparation of PANI Thin Film on Substrate

Figure 1B:
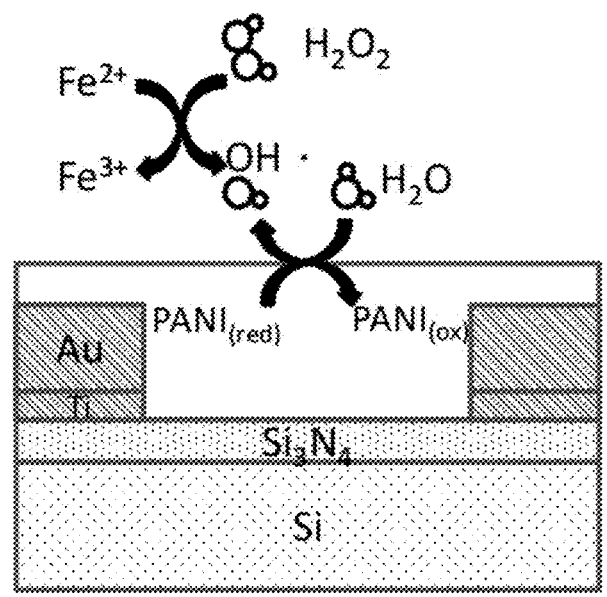
FIG. 1b illustrates the process steps for the reaction between PANI and hydroxyl radicals.
Figure 1C:
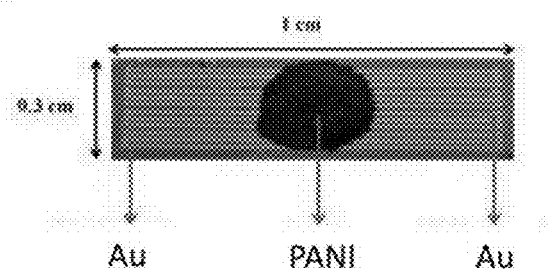
FIG. 1c illustrates the top view photography of the PANI-coated microchip.
Figure 2A:
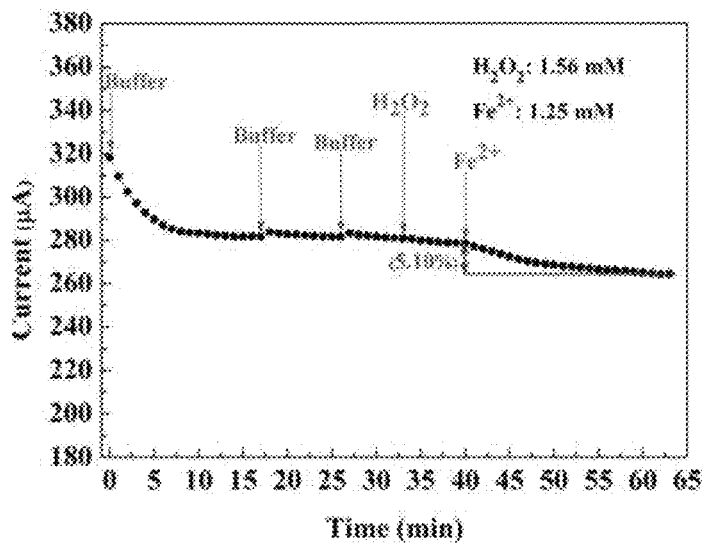
FIGS. 2a to 2d illustrates real time detection of hydroxyl radicals generated by Fenton reaction using Fenton reagents.
Figure 2B:
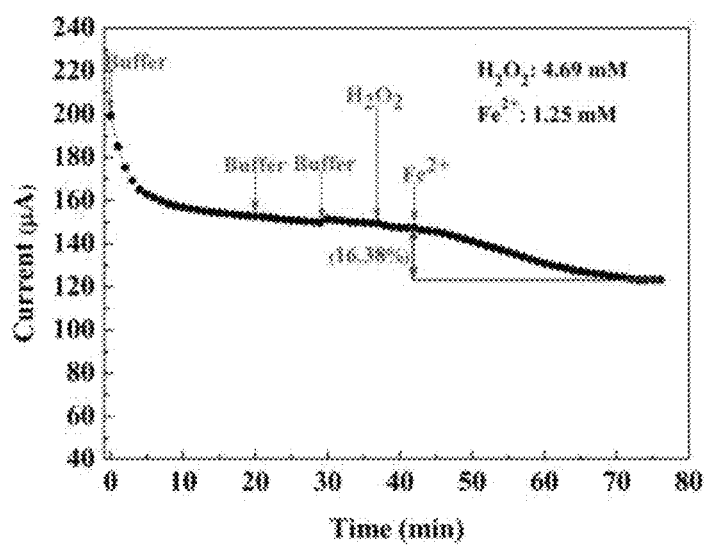
Figure 2C:
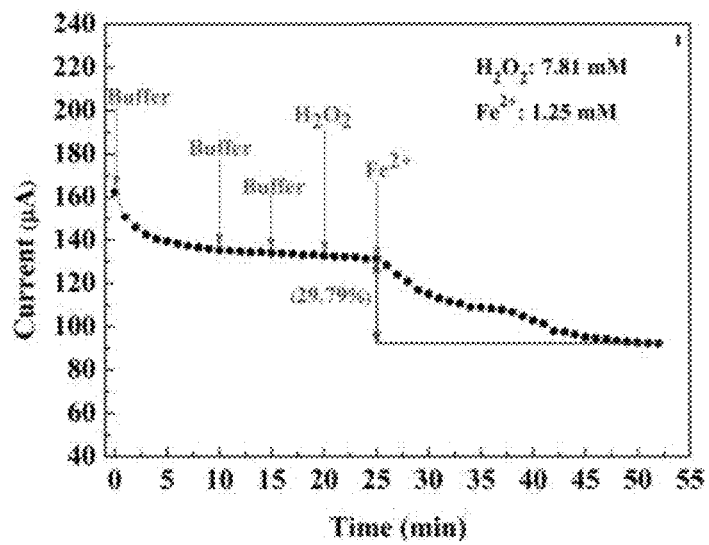
Figure 2D:
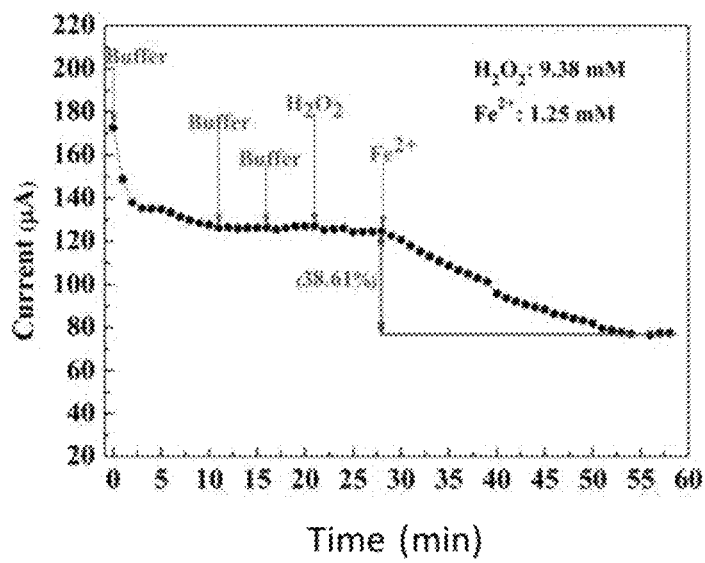

The microchip consists of two metal electrodes made by 200 Å Ti and 1000 Å Au deposited with an e-beam evaporator on a $Si_3N_4$/Si substrate. The length and the width of the Au electrodes are 500 μm and 100 μm, respectively. The gap between the two metal electrodes is 10 μm. Polyaniline emeraldine base was purchased from Headway Advanced Materials Inc. (cat. # ICP-723). Polyaniline was centrifuged until a clear aqua layer was observed. The aqua layer was then carefully removed. 2 mg of the remaining polyaniline was then mixed with 250 μl of de-ionized water thoroughly. The prepared polyaniline solution was then coated on the chip and covered the gap between electrodes. The PANI-coated chip was then baked on a hotplate at 100° C. for 20 minutes. The PANI/Au interface was confirmed to be ohmic contact by measuring the current-voltage characteristics of the device. FIG. 1b shows that the process steps for the reaction between PANI and hydroxyl radicals. FIG. 1c shows the top view photography of the PANI-coated microchip.

Fenton Reaction and Hydroxyl Radicals

The hydroxyl radical was generated from Fenton reaction as shown below in reaction 1:

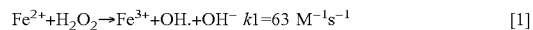

$$Fe^{2+}+H_2O_2 \rightarrow Fe^{3+}+OH.+OH^- \quad k1=63\ M^{-1}s^{-1} \qquad [1]$$

Both iron sulfate heptahydrate (cat. #7782-63-0) and hydrogen peroxide (cat. #7722-84-1) were purchased from Sigma. The iron sulfate heptahydrate was dissolved in 10 mM citric acid/20 mM disodium phosphate buffer solution (pH=7.4) to generate ferrous ion. The hydrogen peroxide was also prepared in the same buffer solution.

Microsensor Measurement

The current of the sensor was measured at a dc bias of 0.1 V at room temperature using an Agilent B1500 parameter analyzer. Firstly, the 10 mM citric acid/20 mM disodium phosphate buffer solution was dropped on the fresh sensor three times and waited until the baseline current level became steady. Hydrogen peroxide solutions prepared in the 10 mM citric acid/20 mM disodium phosphate buffer solution were directly dropped on the surface of PANI layer, followed by adding ferrous ion solutions. Different target concentrations of hydrogen peroxide, including 1.56 mM, 3.13 mM, 4.69 mM, 6.25 mM, 7.81 mM, and 9.38 mM, were measured, at a fixed ferrous ion concentration. The significant current changes of the sensors were observed when the ferrous ion solution was added, indicating that the signal resulted from the appearance of hydroxyl radicals generated from Fenton reaction.

Fluorescence from Oxidation of Amplex Ultrared by Hydrogen Peroxide Via HRP

The Amplex ultrared can react with hydrogen peroxide in the presence of HRP to produce highly fluorescent resorufin. Both Amplex ultrared and HRP were prepared in the 10 mM citric acid/20 mM disodium phosphate buffer solution. 50 µM Amplex ultrared was mixed with different concentrations of hydrogen peroxide in the presence of 2.95 units/mL HRP. The concentration of hydrogen peroxide ranged from 0.1 to 1 µM. The excitation and emission wavelength of Amplex ultrared are 540 nm and 590 nm, respectively. The fluorescence intensities of the oxidized Amplex ultrared were measured with plate reader after 25-minute reaction. Because the amount of the dye was excess compared to that of hydrogen peroxide, hydrogen peroxide was fully consumed, thereby generating the equivalent oxidized dye. The fluorescence intensity versus the concentration of hydrogen peroxide is shown and the calibration curve is used to quantify the concentration of the oxidized dye.

Fluorescence from Oxidation of Amplex Ultrared by Hydroxyl Radicals

The hydroxyl radical solution was prepared to react with Amplex ultrared. It was reported that the hydroxyl radicals can oxidize Amplex ultrared, and the oxidized dye can generate fluorescence emission. By comparing the wavelength of the fluorescence from the dye oxidized by hydroxyl radicals with that of the dye oxidized by hydrogen peroxide via the catalysis of HRP, it was confirmed that both mechanisms produce the same oxidized form of the dye. Therefore, the intensity of the fluorescence produced from the reaction between the hydroxyl radicals and the dye, can be utilized to find out the equivalent concentration of hydroxyl radicals, by using the calibration curve resulted from the fluorescence that was generated from the oxidation of the dye by hydrogen peroxide with HRP. 50 µM Amplex ultrared was prepared to react with hydroxyl radical, which was generated by Fenton reagents. The target concentrations of hydrogen peroxide were the same as the ones that were tested with the PANI sensors, including 1.56 mM, 3.13 mM, 4.69 mM, 6.25 mM, 7.81 mM and 9.38 mM $H_2O_2$, at a fixed target concentration of ferrous ion as 1.25 mM. Amplex ultrared, hydrogen peroxide and ferrous ion were all prepared in the 10 mM citric acid/20 mM disodium phosphate buffer solution. The fluorescence emission of the oxidized Amplex ultrared at 590 nm was measured with the plate reader after 25-minute reaction.

The real time detection of hydroxyl radicals generated by Fenton reaction, using Fenton reagents, including fixed ferrous ion at 1.25 mM and hydrogen peroxide at 1.56 mM, 3.13 mM, 4.69 mM, 6.25 mM, 7.81 mM, and 9.38 mM, at constant bias of 100 mV with fresh sensors, FIGS. 2a, 2b, 2c and 2d show the real time detection of hydroxyl radicals for hydrogen concentrations at 1.56 mM, 3.13 mM, 4.69 mM, 6.25 mM, 7.81 mM, and 9.38 mM, respectively, at fixed ferrous ion concentration ($Fe^{2+}$=1.25 mM). The time interval between two continuous data points is 1 min.

The sensor was initially measured in the air ambient followed by dropping buffer solution. The current gradually decreased after the initial drop of the buffer solution and became steady after a while. Keeping dropping the buffer solution twice did not change the current level any more, indicating the stability of the PANI in the buffer solution. Similar real time detection of hydroxyl radicals via Fenton reaction with the concentration of hydrogen peroxide at 3.13 mM and 6.25 mM, in the presence of ferrous ion at 1.25 mM (not illustrated).

As illustrated in FIGS. 2a, 2b, 2c and 2d, it is obviously observed that hydrogen peroxide do not affect the conductivity of the PANI in the absence of ferrous ions. The current started to decrease only when ferrous ion was added into the hydrogen peroxide solution on the sensor surface. This result demonstrated that the conductivity change of the PANI was attributed to the existence of hydroxyl radicals, which was generated by Fenton reagents. We have also tested the sensors by dropping ferrous ion solution on sensor prior to adding hydrogen peroxide. The result showed that the baseline current of the sensor did not change at all due to adding ferrous ions, until hydrogen peroxide was added (not illustrated). These results excluded the possibility that either only ferrous ions or only hydrogen peroxide could interact with the PANI, thereby changing the conductivity.

Figure 3:
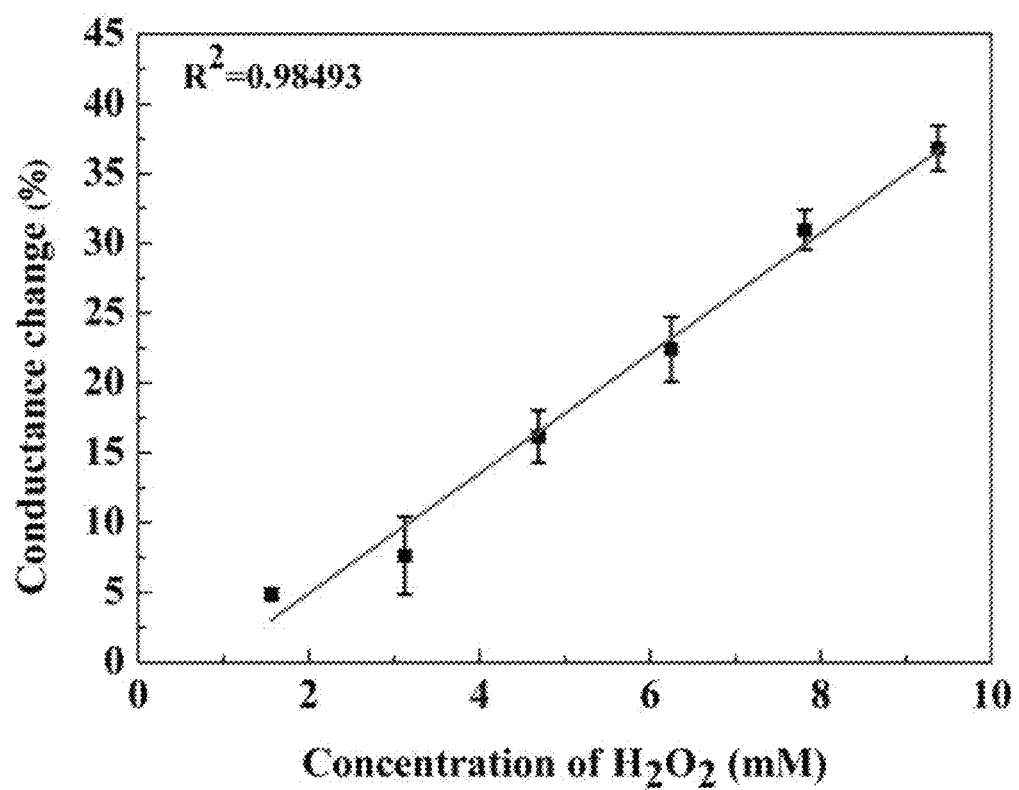
FIG. 3 illustrates the average percentage and the error bar (standard deviation) of the conductivity change rate of PANI versus different hydrogen peroxide concentrations.

FIG. 3 shows the percentage of the conductivity change of PANI versus different hydrogen peroxide concentrations, including 1.56 mM, 3.13 mM, 4.69 mM, 6.25 mM, 7.81 mM, and 9.38 mM, in Fenton reaction. Four fresh sensors were measured for each concentration of hydrogen peroxide. The average and the error bar of the percentage of the conductivity change were calculated for each concentration of hydrogen peroxide. Although different sensors may have different initial currents, the percentage of the conductivity change of PANI was shown to be strongly and linearly dependent on the concentration of hydrogen peroxide, in the presence of ferrous ions.

In order to elucidate the concentration of hydroxyl radical generated in Fenton reaction, the fluorescence spectroscopy was used to assist the establishment of the calibration curve. The dye, Amplex ultrared was utilized to be oxidized by hydrogen peroxide via the catalytic effect of HRP. The oxidized dye can give a strong fluorescence emission at 590 nm. The original dye is inactive in fluorescence emission, and thus did not interfere the fluorescence emission from the oxidized dye. Since the dye can also be oxidized by hydroxyl radical, there should be fluorescence emission from the oxidized dye, as long as the radical-oxidized dye is the same as the one oxidized by hydrogen peroxide. By comparing the fluorescence intensities of hydrogen peroxide-oxidized and radical-oxidized dyes, the concentration of hydroxyl radicals can be resolved.

Figure 4A:
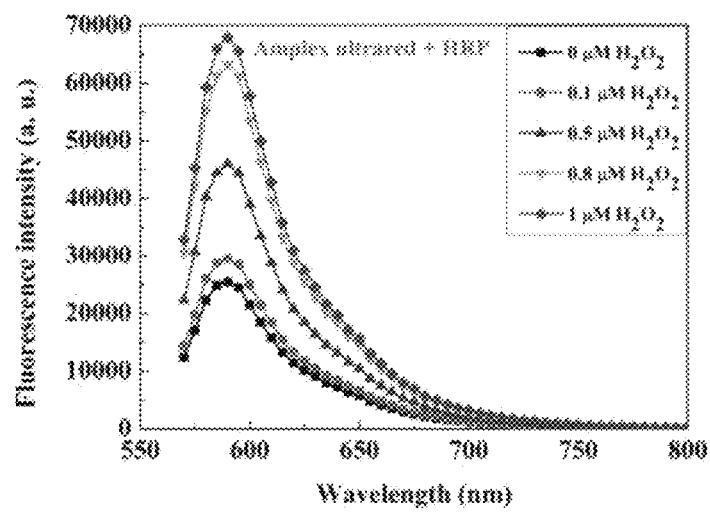
FIG. 4a illustrates the fluorescence emission at 590 nm of oxidized Amplex ultrared via the catalytic effect of HRP, for sample solutions with different concentrations of hydrogen peroxide.
Figure 4B:
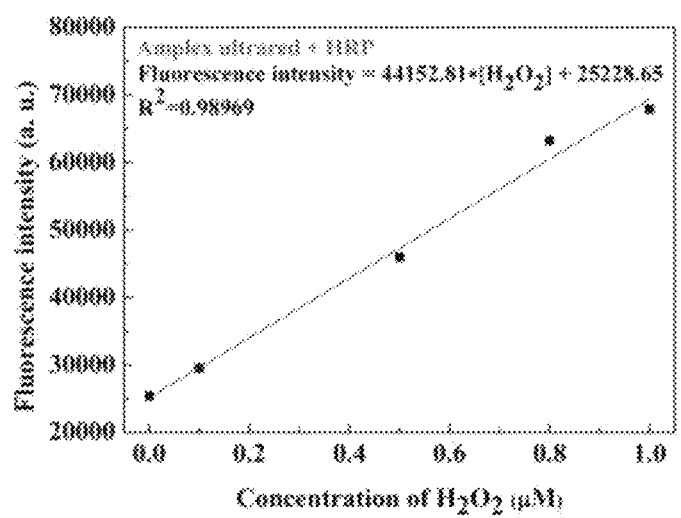
FIG. 4b illustrates the fluorescence intensity (from FIG. 4a) in the presence of HRP versus the concentration of hydrogen peroxide.

To do this, a calibration curve for fluorescence intensity versus the hydrogen peroxide concentration will need to be established first. FIG. 4a shows the fluorescence emission of Amplex ultrared, which was oxidized by hydrogen peroxide via the catalytic effect of HRP, for sample solutions with different concentrations of hydrogen peroxide. Excess Amplex ultrared (50 µM) was prepared to react with limited amount of hydrogen peroxide (0.1 µM, 0.5 µM, 0.8 µM, and 1 µM). Due to the relatively small amount of hydrogen peroxide, compared to the dye concentration, we can therefore assume that the amount of oxidized Amplex ultrared is equal to the total amount of the hydrogen peroxide. FIG. 4b shows the fluorescence intensity (from FIG. 4a) versus the concentration of hydrogen peroxide. The result shows a very good linear dependence of the fluorescence on the concentration of hydrogen peroxide. The line fitted with row data in the FIG. 4b shows a very good linear regression. The fitted line, the mathematical linear equation, is used as a standard calibration curve that can convert fluorescence intensity into the effective concentration of the oxidized dye, which can be used to calibrate the concentration of hydroxyl radicals.

Figure 4C:
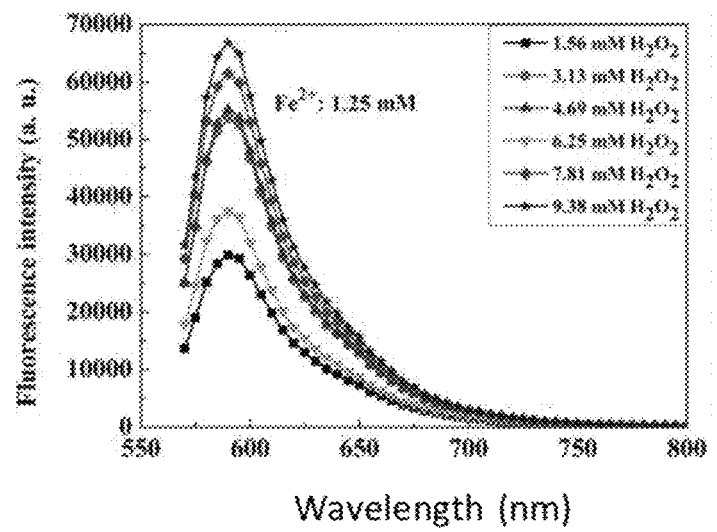
FIG. 4c illustrates the fluorescence emission at 590 nm of Amplex ultrared, which was oxidized by hydroxyl radicals generated by Fenton reaction.
Figure 4D:
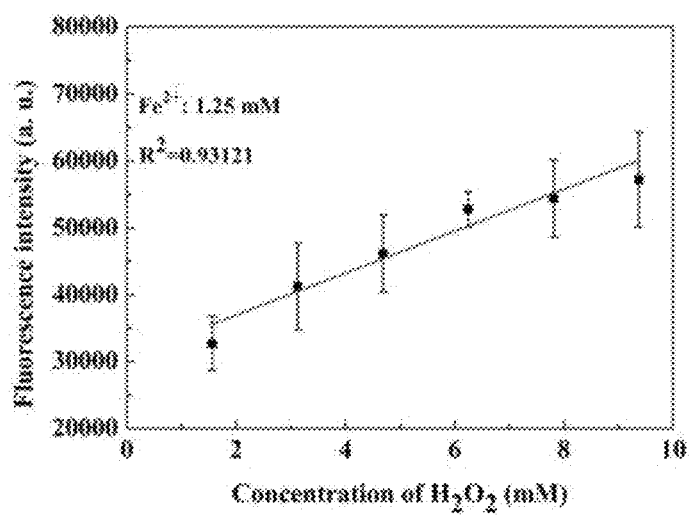
FIG. 4d illustrates the fluorescence emission at 590 nm of oxidized Amplex ultrared in the presence of hydroxyl radicals versus the concentration of hydrogen peroxide.

FIG. 4c shows the fluorescence emission of Amplex ultrared, which was oxidized by hydroxyl radicals generated by Fenton reaction, for sample solutions with different concentrations of hydrogen peroxide. The different concentrations of Fenton reagents in the fluorescence spectra were the same as the concentration of the reagents used on the PANI microsensors. FIG. 4d shows that the fluorescence intensity (from FIG. 4c) versus the concentration of hydrogen peroxide in Fenton reaction, at constant concentration of ferrous ions. Four fresh sensors were measured for each concentration of hydrogen peroxide shown in FIG. 4d, and the average and the error bar (standard deviation) were calculated. The fluorescence intensity measured in Fenton reaction was converted into the concentration of hydroxyl radicals, using the formula extracted from FIG. 4b. The concentration of hydroxyl radicals can thereby be elucidated in different concentrations of hydrogen peroxide prepared in Fenton reaction.

Figure 5:
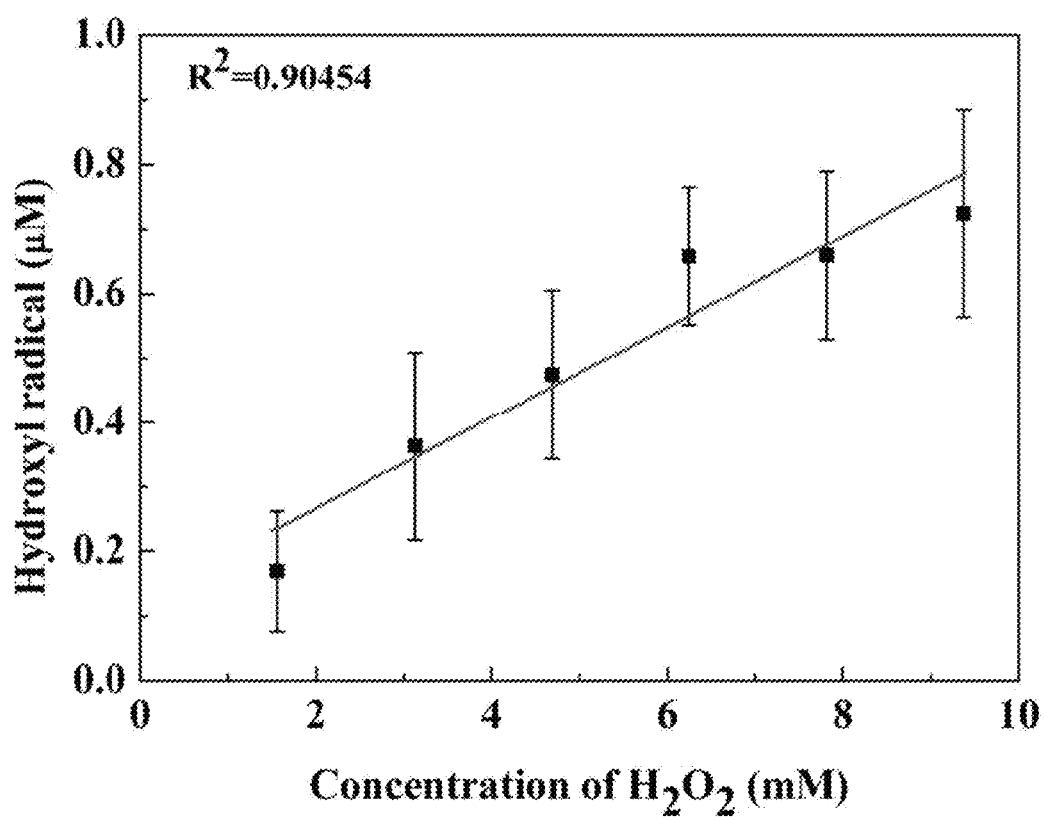
FIG. 5 illustrates correlation between the concentration of hydroxyl radicals and the concentration of hydrogen peroxide in Fenton reaction.
Figure 6:
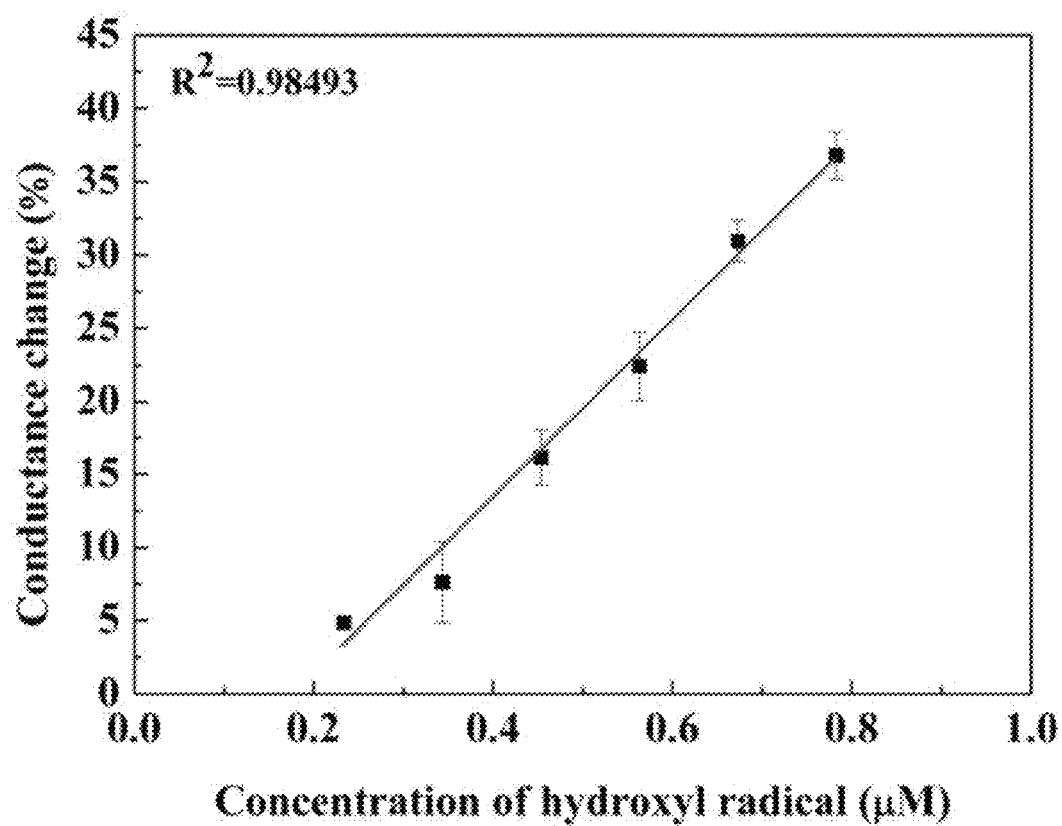
FIG. 6 illustrates correlation between the conductivity change rate of PANI and concentration of hydroxyl radicals.

FIG. 5 gives us important information, including the concentration and the amount of the hydroxyl radicals generated in Fenton reaction, during the detection of hydroxyl radicals by using our electronic microsensors. If we combine FIG. 3 and FIG. 5, the dependence of the percentage of conductivity change of the microsensors on the concentration of hydroxyl radicals can be found, as shown in FIG. 6. In FIG. 6, the x-axis is from the line fitted in FIG. 5, which represents the concentration of hydroxyl radicals in Fenton reaction. The y-axis in FIG. 6 is simply from the y-axis of FIG. 3. FIG. 6 shows the percentage of the conductivity change rate of PANI versus the concentration of hydroxyl radicals in Fenton reaction. The final calibration curve for our hydroxyl sensor is therefore obtained as shown in FIG. 6. The percentage of the conductivity change rate of PANI is linearly dependent on the concentration of hydroxyl radicals. The detectable range of the concentration of the hydroxyl radicals is from 0.2 μM to 0.8 μM. The limit of detection is around 0.2 μM and the conductivity change rate of PANI is greater than 5%. The result shows that this electronic hydroxyl radical microsensor has comparable sensitivity and limit of detection to some frequently used techniques, such as the fluorescence spectroscopy, ESR, or UV-Vis (absorbance).

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A method for measuring free radical, comprising:
   providing a sensor including a substrate and a conductive polymer layer, wherein the conductive polymer layer is configured on the substrate and essentially made of a conductive polymer, wherein the conductive polymer comprises polyacetylene, polyparaphenylene, polythiophene, polyfuran, polythianaphthene or polyaniline (PANI), wherein the sensor further comprises a first electrode and a second electrode, and wherein the conductive polymer layer is electrically connected between the first electrode and the second electrode;
   applying a liquid sample with a free radical to the sensor so that the conductive polymer layer is covered with the liquid sample and the conductivity of the conductive polymer layer is lowered due to oxidation of the conductive polymer by the free radical; and
   calculating the concentration of the free radical in the liquid sample based on the conductivity change rate of the conductive polymer before and after the liquid sample is applied to the conductive polymer.

2. The method for measuring free radical as claimed in claim 1, further comprising:
   measuring a first conductivity and a second conductivity of the conductive polymer layer, wherein the first conductivity is the conductivity of the conductive polymer layer before applied with the liquid sample with free radical and the second conductivity is the conductivity of the conductive polymer layer after applied with the liquid sample with free radical, and the conductivity change rate of the conductive polymer is based on the change rate of the first conductivity and the second conductivity.

3. The method for measuring free radical as claimed in claim 2, wherein the measuring the first conductivity and the second conductivity of the conductive polymer layer is obtained by applying a bias to the conductive polymer layer and measuring a current of the conductive polymer layer.

4. The method for measuring free radical as claimed in claim 3, wherein the bias is applied to the first electrode and the second electrode.

5. The method for measuring free radical as claimed in claim 1, wherein the conductive polymer is polyaniline.

6. The method for measuring free radical as claimed in claim 1, wherein the surface of the conductive polymer is modified with propane sultone.

7. The method for measuring free radical as claimed in claim 1, wherein the free radical is a reactive oxygen species.

8. The method for measuring free radical as claimed in claim 1, wherein the free radical is a hydroxyl radical.

9. The method for measuring free radical as claimed in claim 1, wherein the concentration of the free radical ranges from 0.2 μM to 0.8 μM.

10. The method for measuring free radical as claimed in claim 1, wherein the conductivity change rate is greater than 5%.

* * * * *